United States Patent
Wang et al.

(10) Patent No.: US 12,144,555 B2
(45) Date of Patent: Nov. 19, 2024

(54) AUGMENTED REALITY-ASSISTED METHOD FOR PERFORMING SURGERY

(71) Applicant: MEDICALTEK CO., LTD., Taichung (TW)

(72) Inventors: Yen-Yu Wang, Taichung (TW); Shu-Jui Hsieh, Taichung (TW); Jing-Ying Huang, Taichung (TW)

(73) Assignee: MEDICALTEK CO., LTD., Taichung (TW)

( * ) Notice: Subject to any disclaimer, the term of this patent is extended or adjusted under 35 U.S.C. 154(b) by 343 days.

(21) Appl. No.: 17/553,880

(22) Filed: Dec. 17, 2021

(65) Prior Publication Data

US 2022/0395328 A1   Dec. 15, 2022

(30) Foreign Application Priority Data

Jun. 11, 2021   (TW) ................................ 110121449

(51) Int. Cl.
 *A61B 34/10*   (2016.01)
 *A61B 34/20*   (2016.01)
 (Continued)

(52) U.S. Cl.
 CPC .............. *A61B 34/10* (2016.02); *A61B 34/20* (2016.02); *A61B 90/37* (2016.02); *G06T 19/006* (2013.01);
 (Continued)

(58) Field of Classification Search
 CPC .............. A61B 34/10–20; A61B 90/37; A61B 2034/105; A61B 2034/107;
 (Continued)

(56) References Cited

U.S. PATENT DOCUMENTS

| | | | |
|---|---|---|---|
| 6,959,215 B2* | 10/2005 | Gliner | A61N 1/36067 607/45 |
| 2018/0092699 A1* | 4/2018 | Finley | A61B 34/20 |
| 2021/0192759 A1* | 6/2021 | Lang | A61C 9/004 |

OTHER PUBLICATIONS

Endoscopic Augmented Reality Navigation System for Endonasal Transsphenoidal Surgery to Treat Pituitary Tumors: Technical Note; Neurosurgery 50(6); p. 1393-1397; Jun. 2002 (Year: 2002).*

* cited by examiner

*Primary Examiner* — Yi-Shan Yang
(74) *Attorney, Agent, or Firm* — Muncy, Geissler, Olds & Lowe, P.C.

(57) ABSTRACT

An augmented reality-assisted method for performing surgery comprises: disposing a position sensing element at a facial positioning point of a patient before craniotomy to obtain skull space and intracranial space information for defining a coordinate space; obtaining a brain anatomical image for constructing a three-dimensional graphic, the graphic comprising a graphic positioning point and a feature associated with a gyrus feature; defining a relative positional relationship between the graphic and the space, aligning the facial positioning point with the graphic positioning point; using a probe to obtain a spatial position of the gyrus feature after craniotomy, using the gyrus feature as a calibration reference point; generating a displacement and rotation parameter based on a coordinate difference of the feature relative to the reference point; adjusting a position and/or an angle of the graphic on a display according to the parameter, and the display displaying the calibrated three-dimensional graphic.

12 Claims, 12 Drawing Sheets

(51) Int. Cl.
*A61B 90/00* (2016.01)
*G06T 19/00* (2011.01)
(52) U.S. Cl.
CPC ... *A61B 2034/105* (2016.02); *A61B 2034/107* (2016.02); *A61B 2034/2055* (2016.02); *A61B 2034/2065* (2016.02); *A61B 2034/2068* (2016.02); *A61B 2090/365* (2016.02); *A61B 2090/367* (2016.02); *A61B 2090/374* (2016.02)
(58) Field of Classification Search
CPC .... A61B 2034/2055; A61B 2034/2068; A61B 2090/365–374
See application file for complete search history.

AUGMENTED REALITY-ASSISTED METHOD FOR PERFORMING SURGERY

FIELD OF THE INVENTION

The invention relates to a computer-assisted method for performing surgery, and more particularly to an augmented reality-assisted method for performing surgery.

BACKGROUND OF THE INVENTION

Craniotomy often causes brain shift after skull opening, and possible causes include physical, surgical, and biological factors. Physical factors such as the patient's posture and gravity during the surgical operation; surgical factors such as the surgical equipment used (e.g. tractor) and loss of body fluids and brain tissues during surgery; and biological factors such as tumor type, location, and drugs used during surgery.

In craniotomy operations, preoperative nuclear magnetic resonance images are generally used in conjunction with surgical navigation system to guide the operation. However, when a brain shift occurs, the surgical navigation reference image becomes no longer accurate, thus increasing the difficulty for doctors to perform the operation.

SUMMARY OF THE INVENTION

The invention provides an augmented reality-assisted method for performing surgery, which is capable of solving the problem of mismatch between the brain in surgery and preoperative images due to brain shift during craniotomy.

In order to achieve the above-mentioned object, the invention provides an augmented reality-assisted method for performing surgery, comprising following steps of: step 1: disposing a position sensing element at a facial positioning point of a target patient to obtain a skull space information and an intracranial space information of the target patient before craniotomy, and defining a coordinate space according to the skull space information and the intracranial space information; step 2: obtaining a brain anatomical image of the target patient before craniotomy and constructing a three-dimensional graphic based on the brain anatomical image, the three-dimensional graphic comprising a graphic positioning point associated with the facial positioning point of the target patient and a feature associated with a gyms feature of the target patient; step 3: defining a relative positional relationship between the three-dimensional graphic and the coordinate space, aligning the facial positioning point with the graphic positioning point of the three-dimensional graphic, and displaying an aligned three-dimensional graphic on a display of an augmented reality device; step 4: using a probe to obtain a spatial position of the gyms feature of the target patient in the coordinate space after craniotomy, using the gyms feature as a calibration reference point; step 5: generating a displacement and rotation parameter based on a coordinate difference of the feature of the three-dimensional graphic relative to the calibration reference point; and step 6: adjusting a position and/or an angle of the three-dimensional graphic on the display according to the displacement and rotation parameter, so that the display displaying the calibrated three-dimensional graphic.

In order to achieve the above-mentioned object, the invention further provides an augmented reality-assisted method for performing surgery, comprising following steps of: step 1: disposing a position sensing element at a facial positioning point of a target patient to obtain a skull and intracranial space information of the target patient before craniotomy, and defining a coordinate space according to the skull and intracranial space information; step 2: obtaining a brain anatomical image of the target patient before craniotomy and constructing a three-dimensional graphic based on the brain anatomical image, the three-dimensional graphic comprising a graphic positioning point associated with the facial positioning point of the target patient and a feature associated with a gyrus feature of the target patient; step 3: defining a relative positional relationship between the three-dimensional graphic and the coordinate space, aligning the facial positioning point with the graphic positioning point of the three-dimensional graphic, and displaying an aligned three-dimensional graphic on a display of an augmented reality device; step 4: capturing a brain image of the target patient after craniotomy to generate a gyms image, displaying the gyms image on the display, the gyms image comprising a gyms feature point, the gyms feature point corresponding to the gyms feature of the brain of the target patient; step 5: calculating a coordinate difference between the gyms feature point of the gyrus image and the feature of the three-dimensional graphic to generate a displacement and rotation parameter; and step 6: adjusting a position and/or an angle of the three-dimensional graphic on the display according to the displacement and rotation parameter, thus displaying the feature of the three-dimensional graphic superimposed on the gyms feature point of the gyrus image on the display.

In order to achieve the above-mentioned object, the invention further provides an augmented reality-assisted method for performing surgery, comprising following steps of: step 1: disposing a position sensing element at a facial positioning point of a target patient to obtain a skull and intracranial space information of the target patient before craniotomy, and defining a coordinate space according to the skull and intracranial space information; step 2: obtaining a brain anatomical image of the target patient before craniotomy and constructing a three-dimensional graphic based on the brain anatomical image, the three-dimensional graphic comprising a graphic positioning point associated with the facial positioning point of the target patient and a feature associated with a gyrus feature of the target patient; step 3: defining a relative positional relationship between the three-dimensional graphic and the coordinate space, aligning the facial positioning point with the graphic positioning point of the three-dimensional graphic, and displaying an aligned three-dimensional graphic on a display of an augmented reality device; step 4: capturing a brain image of the target patient after craniotomy to generate a gyms image and a depth image information, displaying the gyms image on the display, the gyms image comprising a gyrus feature point, the gyrus feature point corresponding to the gyms feature of the brain of the target patient; step 5: constructing a first curved grid based on the three-dimensional graphic, and constructing a second curved grid based on the gyrus image and the depth image information, the first curved grid comprising the feature associated with the gyms feature of the target patient, the second curved grid comprising a grid positioning point associated with the gyms feature of the target patient; step 6: calculating a difference between the first curved grid and the second curved grid and performing an adjustment on the first curved grid, so that a minimum distance being between the feature of the first curved grid and the grid positioning point of the second curved grid; and step 7: the display displaying the superimposed gyrus image.

Based on the foregoing, the augmented reality-assisted method for performing surgery of the invention are capable of adjusting or calibrating the three-dimensional graphic in real time, so as to compensate the mismatch between the brain and preoperative images to display images more accurately, and the system based on the augmented reality-assisted method is capable of providing calibrated images in real time and accurately, and can be used, for example, in supporting medical treatment, surgery, or operating instruments.

In order to make the above-mentioned features and advantages of the invention more obvious and comprehensible, the following specific embodiments are described in detail in conjunction with the accompanying drawings.

DETAILED DESCRIPTION OF THE PREFERRED EMBODIMENTS

The foregoing and other technical content, features and efficacies of the invention will be clearly presented in the following detailed description of the preferred embodiments with reference to the drawings.

Figure 1:
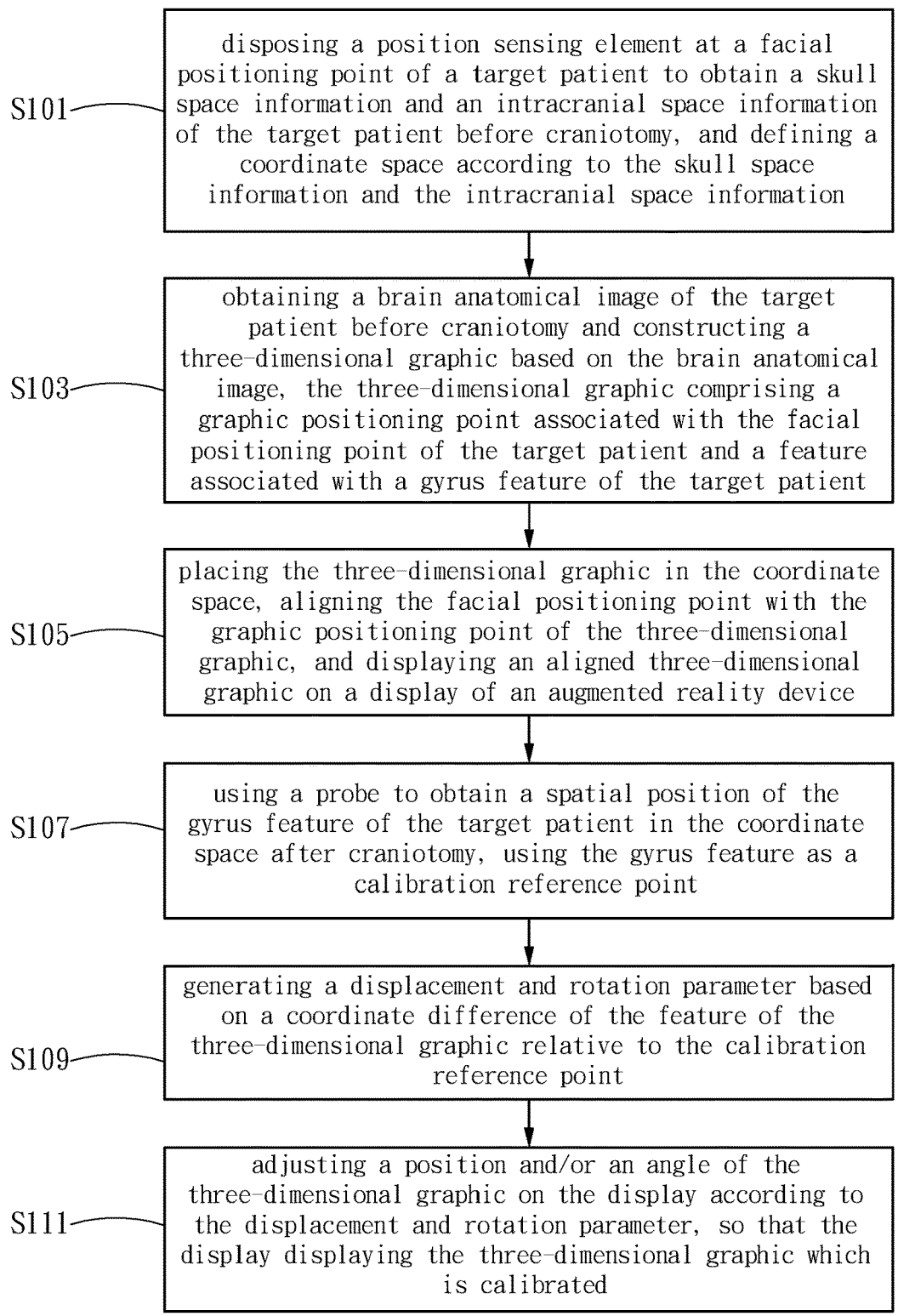
FIG. 1 is a flowchart of a method according to an embodiment of the invention.
Figure 2:
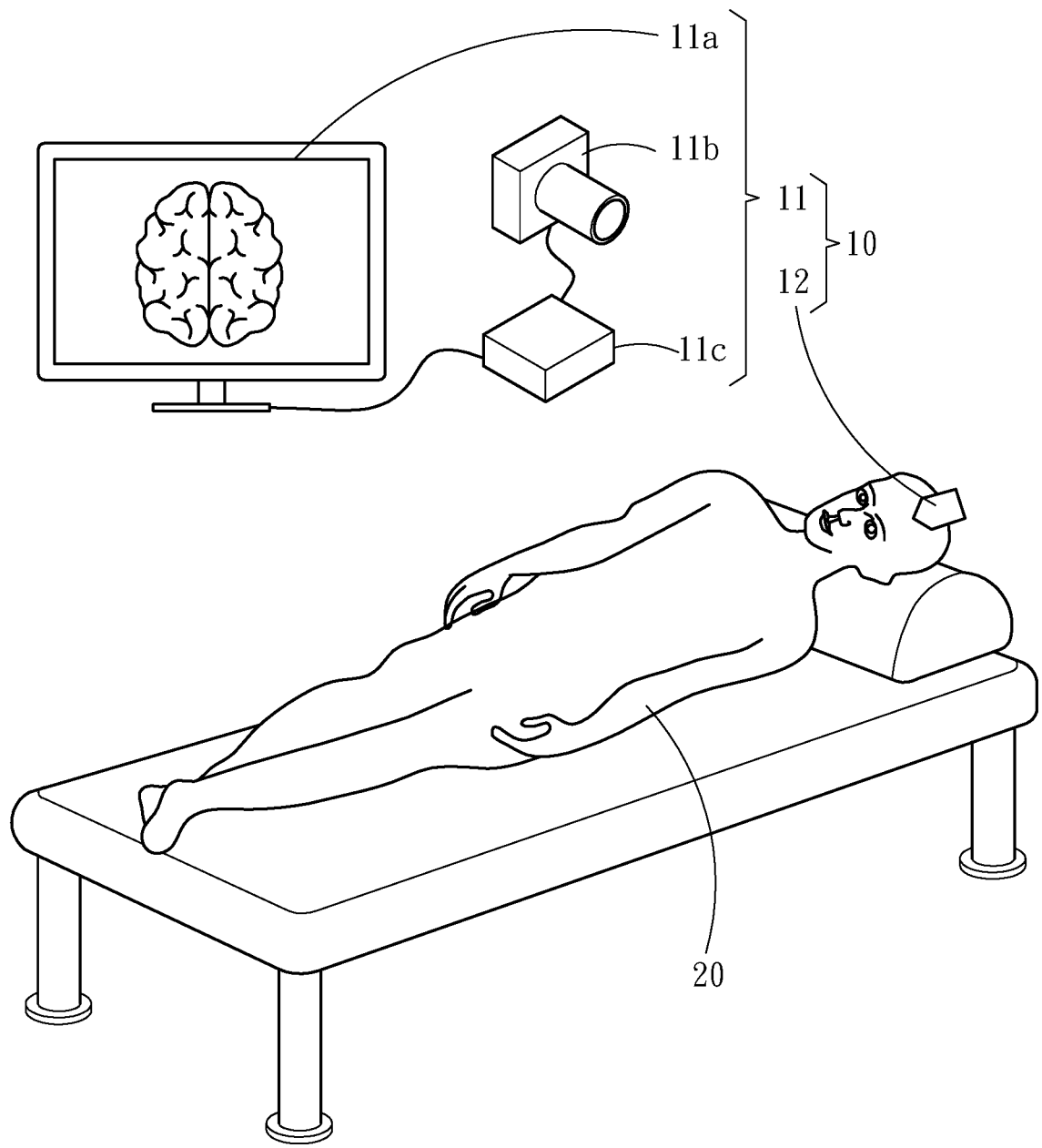
FIG. 2 is a schematic diagram of a system according to an embodiment of the invention.

Please refer to FIG. 1 and FIG. 2, FIG. 1 is a flowchart of a method according to an embodiment of the invention; and FIG. 2 is a schematic diagram of a system according to an embodiment of the invention. An augmented reality-assisted system 10 method for performing surgery depicted in FIG. 2 comprises an augmented reality device 11, and a position sensing element 12 for applying to a target patient 20. The augmented reality device 11 comprises a display 11a, an image capturing device 11b, and a processing device 11c. In this embodiment, the position sensing element 12 is a positioning element used in surgical navigation, for example, an electromagnetic induction tracking element or an optical tracking element.

In this embodiment, a craniotomy for the target patient 20 is taken as an example. A method 100 comprises following steps.

Figure 3:
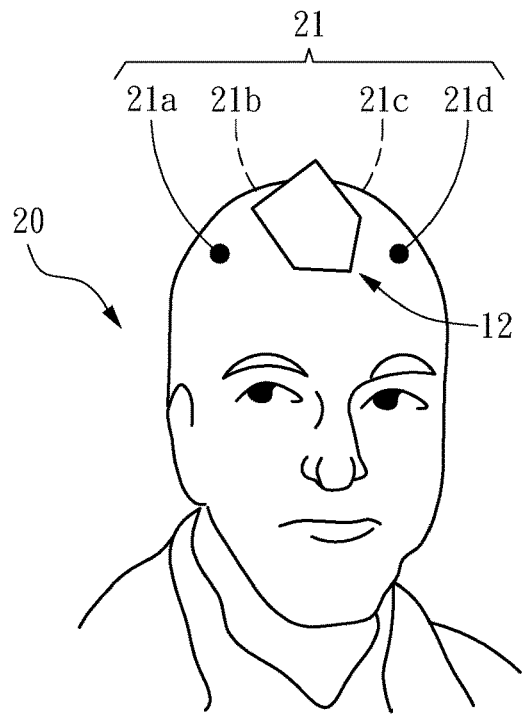
FIG. 3 is a schematic diagram of disposing a position sensing element at a facial positioning point of a target patient according to an embodiment of the invention.

In step S101, referring to FIG. 3, before performing the craniotomy, disposing the position sensing element 12 on at least one facial positioning point 21 of the target patient 20 to obtain a skull space information and an intracranial space information of the target patient 20 before the craniotomy. The facial positioning point 21 can be a predetermined specific position on a head of the target patient 20 before the craniotomy for performing subsequent information acquisition operations. In this embodiment, the facial positioning point 21 comprises a first facial positioning point 21a, a second facial positioning point 21b, a third facial positioning point 21c, and a fourth facial positioning point 21d.

Figure 4:
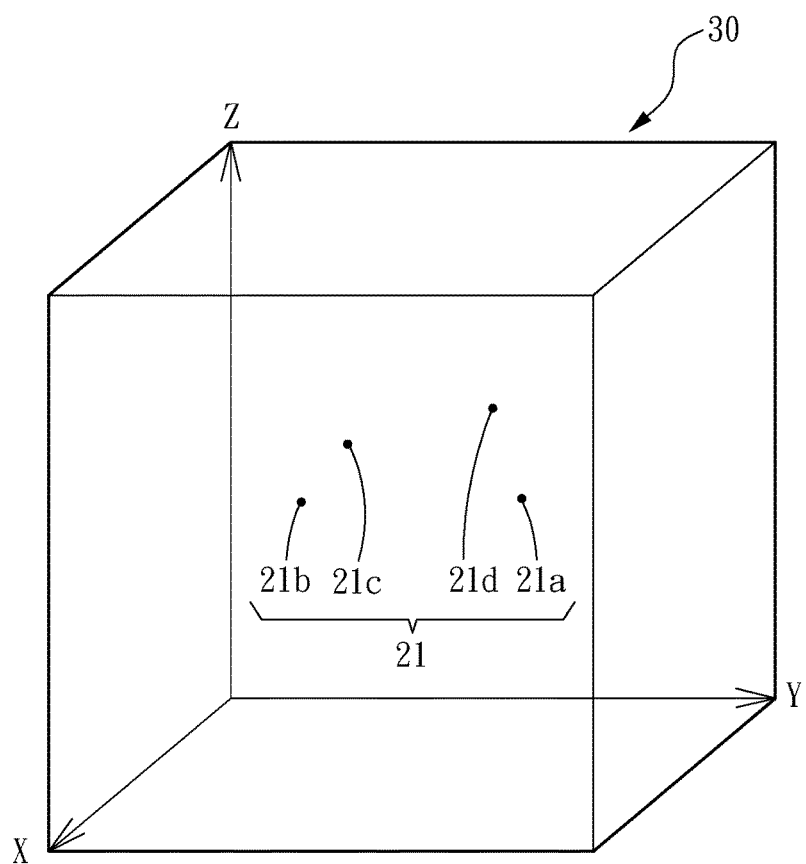
FIG. 4 is a schematic diagram of a coordinate space according to an embodiment of the invention.

The skull space information can be, for example, information of size, structure, or contour of a skull of the target patient 20, and the intracranial space information can be, for example, information of size, structure, or contour of a cranial cavity of the target patient 20. Then, defining a coordinate space 30 using the processing device 11c based on the skull space information and the intracranial space information, as shown in FIG. 4. The coordinate space 30 corresponds to an intracranial space of the target patient 20, that is, the facial positioning point 21 is located at a specific position in the coordinate space 30.

Figure 5:
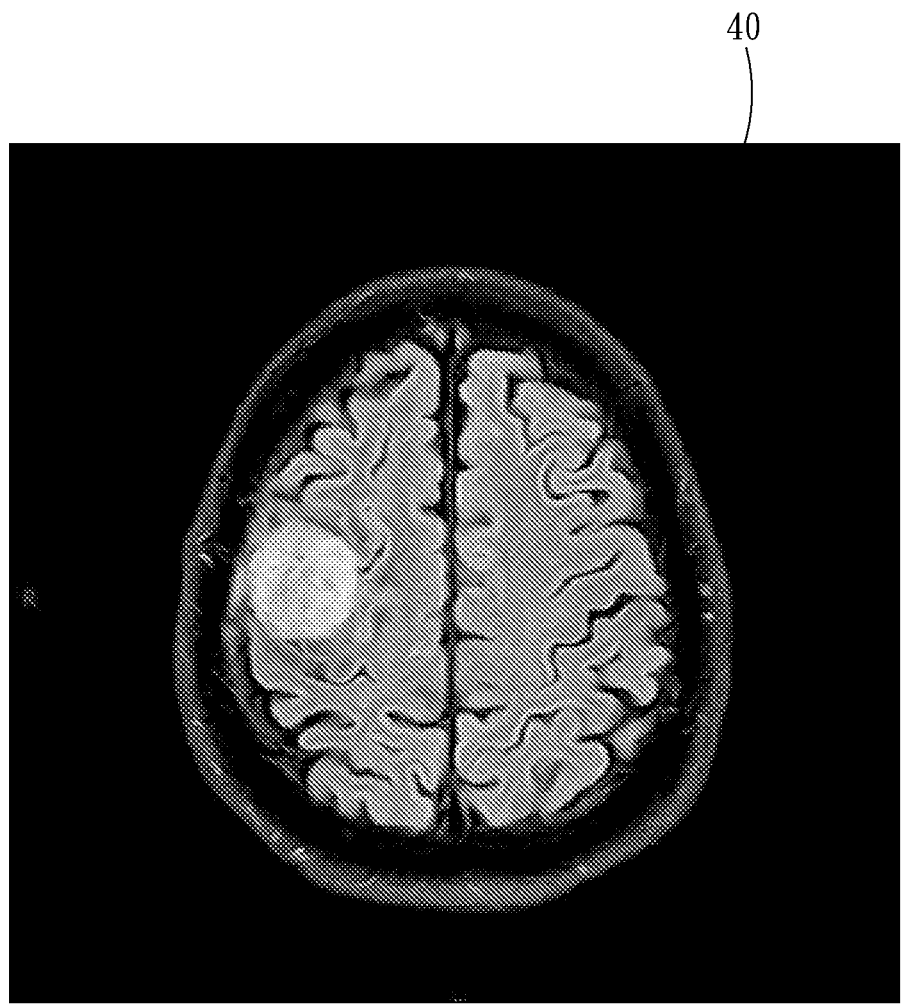
FIG. 5 is a brain anatomical image according to an embodiment of the invention.
Figure 6:
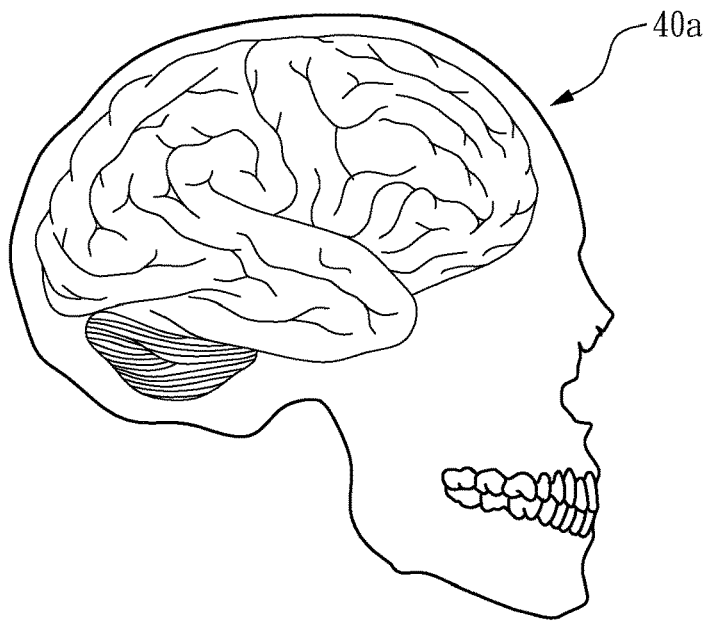
FIG. 6 is a schematic diagram of a three-dimensional graphic according to an embodiment of the invention.
Figure 7:
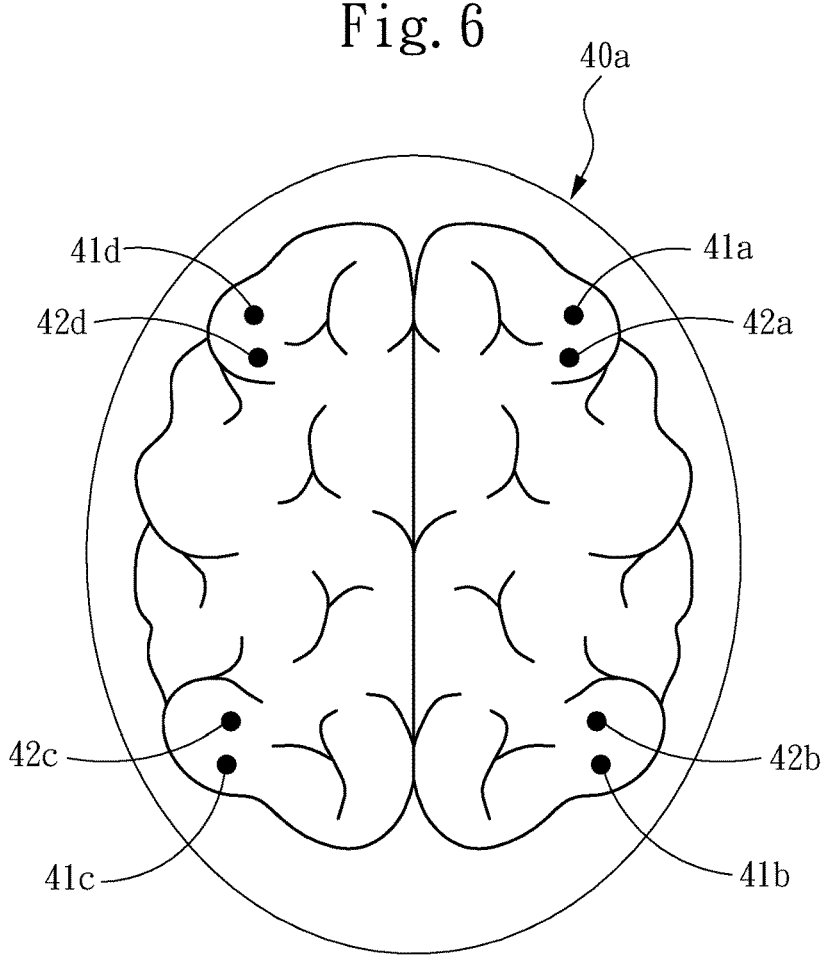
FIG. 7 is a schematic diagram of graphic positioning points and gyrus features of the target patient according to an embodiment of the invention.

In step S103, obtaining a brain anatomical image 40 of the target patient 20 before the craniotomy, as shown in FIG. 5. In this embodiment, the brain anatomical image 40 is Nuclear Magnetic Resonance Imaging (NMRI), while in other embodiments, the brain anatomical image 40 can also be an X-ray image or a computed tomography image. Constructing a three-dimensional graphic 40a using the processing device 11c according to the brain anatomical image 40, as shown in FIG. 6. The three-dimensional graphic 40a can be regarded as a virtual intracranial three-dimensional model of the skull of the target patient 20. According to image features in the three-dimensional graphic 40a, associating the facial positioning point 21 of the target patient 20 with at least one graphic positioning point in the three-dimensional graphic 40a, and associating at least one gyrus feature of the target patient 20 with at least one feature in the three-dimensional graphic 40a, as shown in FIG. 7. In this embodiment, the graphic positioning point comprises a first graphic positioning point 41a, a second graphic positioning point 41b, a third graphic positioning point 41c, and a fourth graphic positioning point 41d, the feature comprises a first feature 42a, a second feature 42b, a third feature 42c, and a fourth feature 42d. Specifically, the graphic positioning point on the three-dimensional graphic 40a can be marked as the facial positioning point 21 of the target patient 20, and the feature in the three-dimensional graphic 40a can be marked as the gyms feature of the target patient 20.

In this embodiment, multi-section nuclear magnetic resonance images are generated by NMRI, and then the three-dimensional graphic 40a is generated through a volume rendering.

Figure 8:
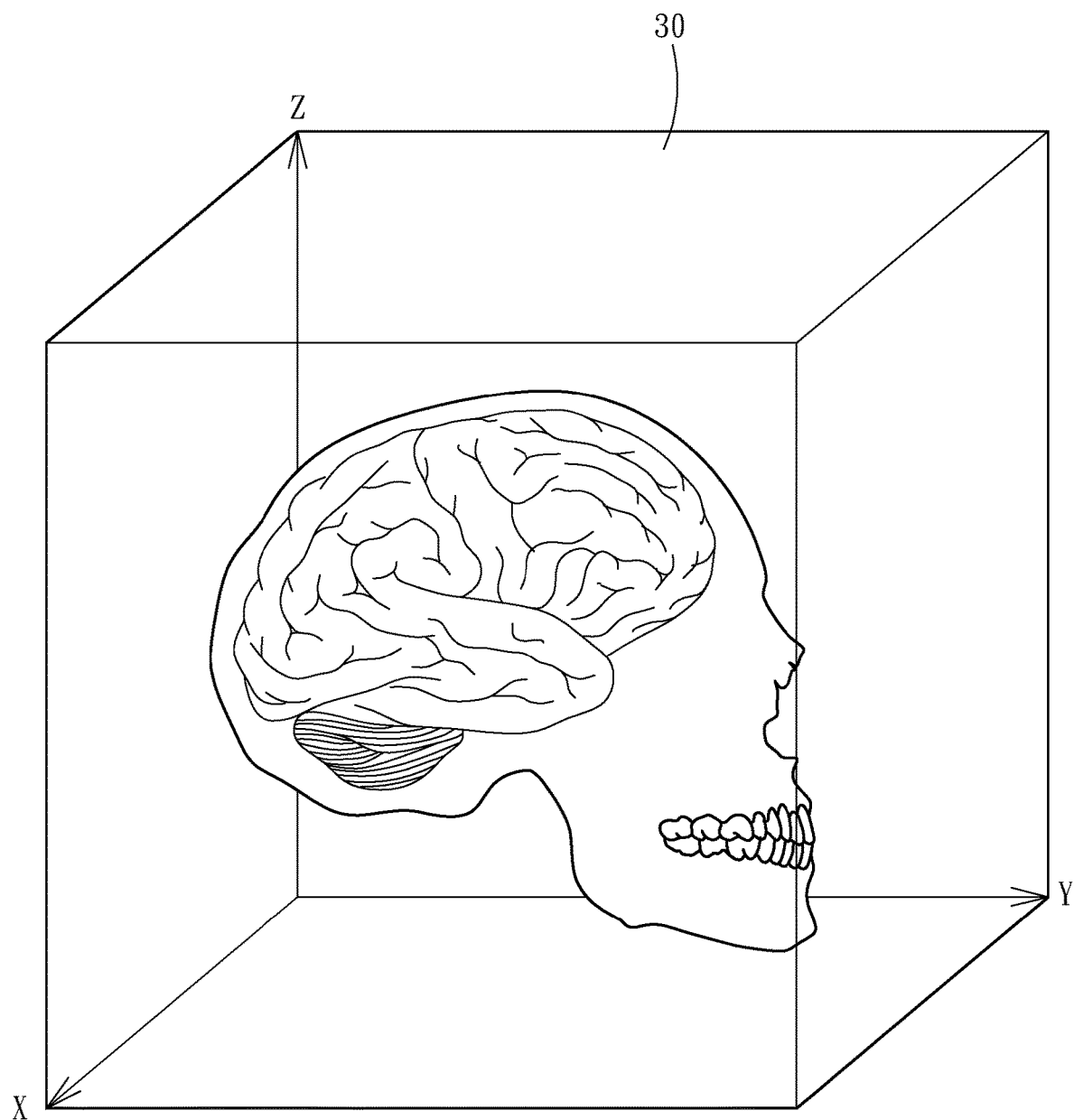
FIG. 8 is a schematic diagram of the three-dimensional graphic being placed in the coordinate space according to an embodiment of the invention.

In step S105, placing the three-dimensional graphic 40a in the coordinate space 30, as shown in FIG. 8, and using the facial positioning point 21 as a positioning reference. In detail, aligning the facial positioning point 21 in the coordinate space 30 with the graphic positioning point of the three-dimensional graphic 40a, that is, the virtual three-dimensional model of the target patient 20 is made to use the coordinate space 30 as a reference coordinate system. And displaying the aligned three-dimensional graphic 40a on the display 11a of the augmented reality device 11.

Figure 9:
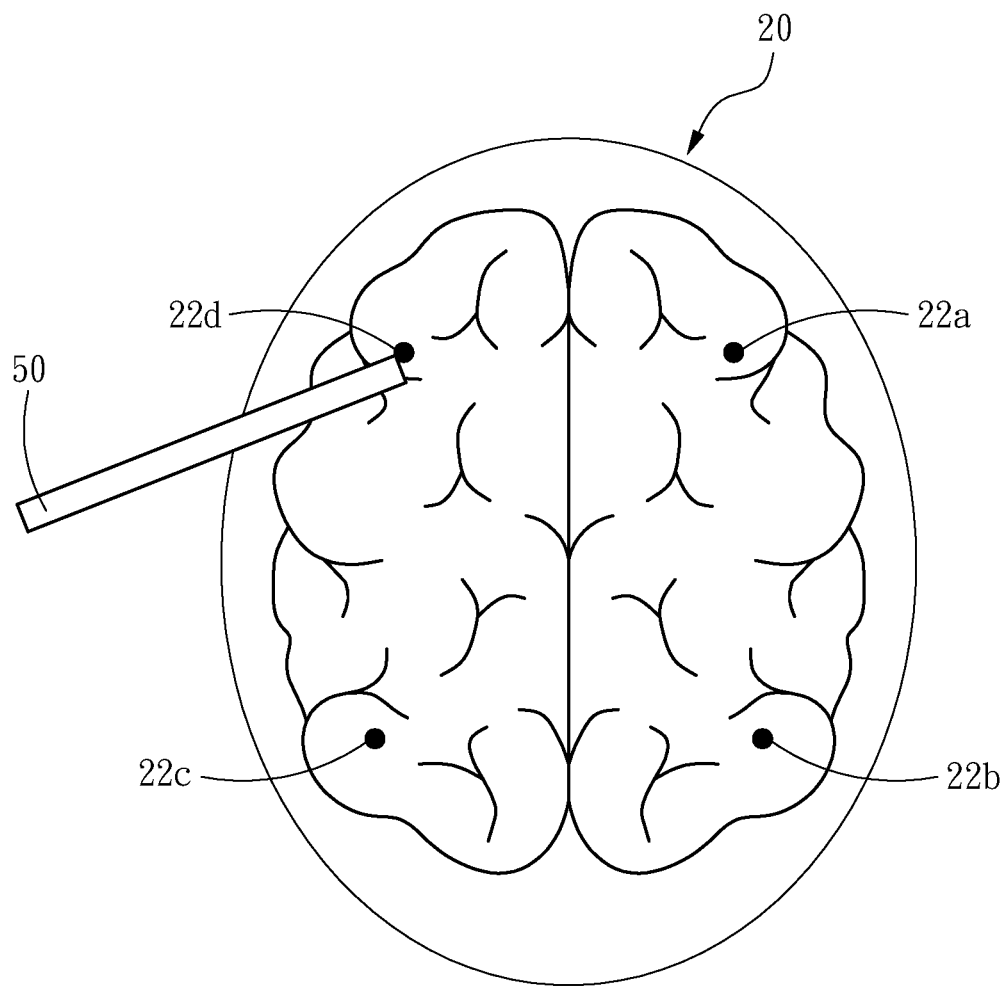
FIG. 9 is a schematic diagram of using a probe to detect a brain entity of the target patient according to an embodiment of the invention.

In step S107, when performing a surgical operation and during a craniotomy, using a probe 50 to detect a brain entity of the target patient 20, as shown in FIG. 9. Obtaining a position of the gyms feature of the brain of the target patient 20 during the surgical operation. In one example, the gyms feature comprises a first gyms feature 22a, a second gyms feature 22b, a third gyms feature 22c, and a fourth gyms feature 22d. Obtaining a spatial position of the gyrus feature in a preset coordinate system, the preset coordinate system can be defined based on the probe 50, and then converting the preset coordinate system into the coordinate space 30 to obtain a position of the gyrus feature in the coordinate space 30. Wherein, the gyms feature is defined as a calibration reference point.

In step S109, due to factors of loss of cerebrospinal fluid, changes in intracranial pressure or gravity in the craniotomy (i.e. after temporarily removing bone from the skull to access the brain), the brain will be displaced and deformed after the craniotomy compared to before the craniotomy. Therefore, there is a spatial mismatch between the gyms feature of the brain during surgery of the target patient 20 and the feature of the three-dimensional graphic 40a. In order to compensate the mismatch, a displacement and rotation parameter is generated based on a coordinate difference of the feature of the three-dimensional graphic 40a relative to the calibration reference point in space. The feature represents the graphic positioning point of the three-dimensional graphic 40a associated with the gyrus feature of the target patient 20, and the calibration reference point is the spatial position of the gyms feature of the target patient 20 in the craniotomy obtained through the probe 50. The displacement and rotation parameter generated through the coordinate difference comprises a coordinate difference between the feature and the calibration reference point. Thereby, the coordinate difference between the feature and the calibration reference point can be calculated for using in subsequent positioning calibration of the three-dimensional graphic 40a.

Figure 10:
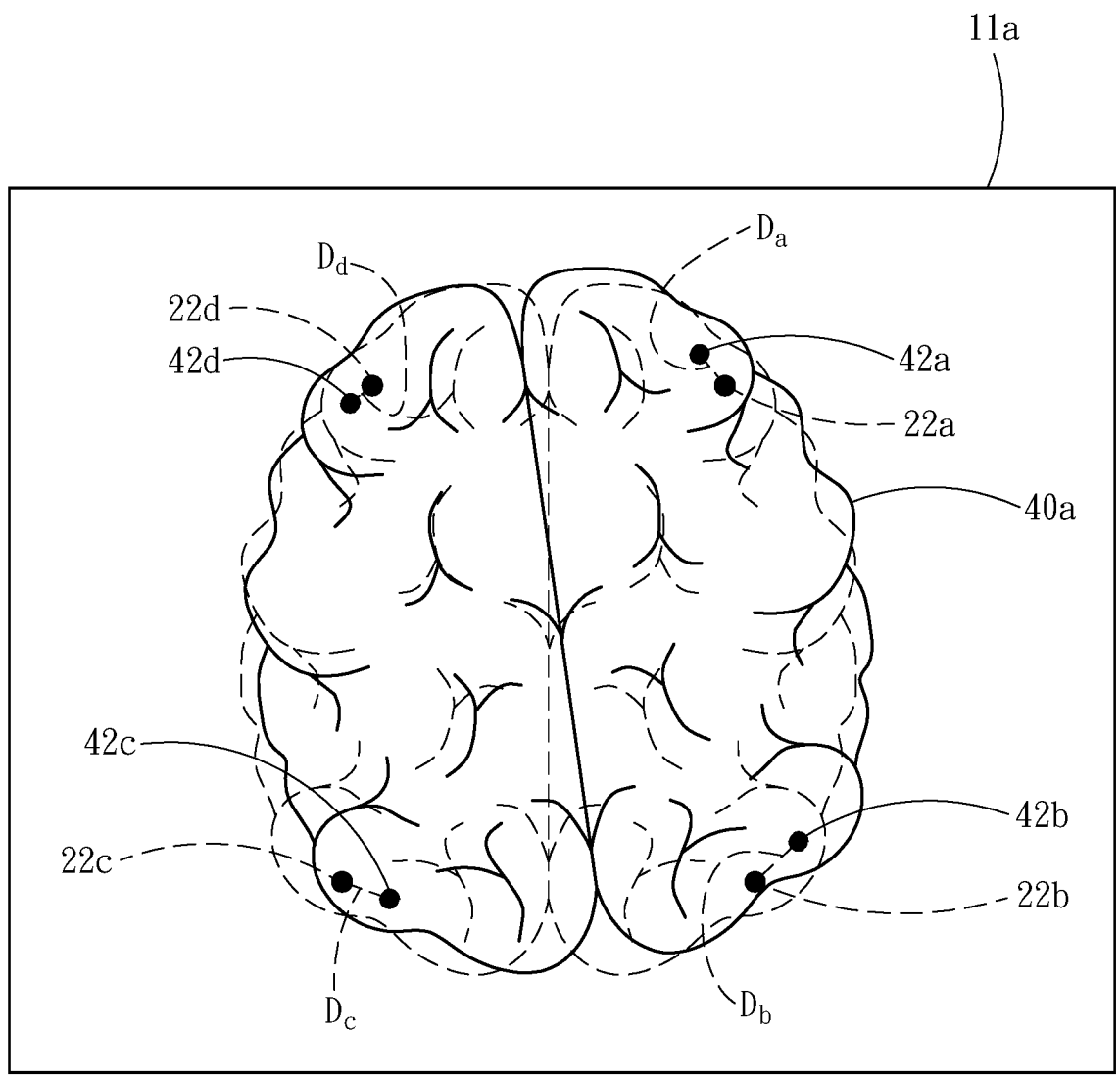
FIG. 10 is a schematic diagram of a display showing the three-dimensional graphic of the target patient according to an embodiment of the invention.

In step S111, adjusting a position and/or an angle of the three-dimensional graphic 40a on the display 11a according to the displacement and rotation parameter, so that the display 11a displaying the calibrated three-dimensional graphic 40a, as shown in FIG. 10, a schematic diagram showing differences before and after calibration, wherein, $D_a$ represents a coordinate difference between the first gyrus feature 22a and the first feature 42a; $D_b$ represents a coordinate difference between the second gyms feature 22b and the second feature 42b; $D_c$ represents a coordinate difference between the third gyrus feature 22c and the third feature 42c; and $D_d$ represents a coordinate difference between the fourth gyrus feature 22d and the fourth feature 42d. Thereby, during a medical treatment operation, the system 10 is capable of calibrating the three-dimensional graphic 40a in real time, so that the display 11a is capable of displaying calibrated images.

Figure 11:
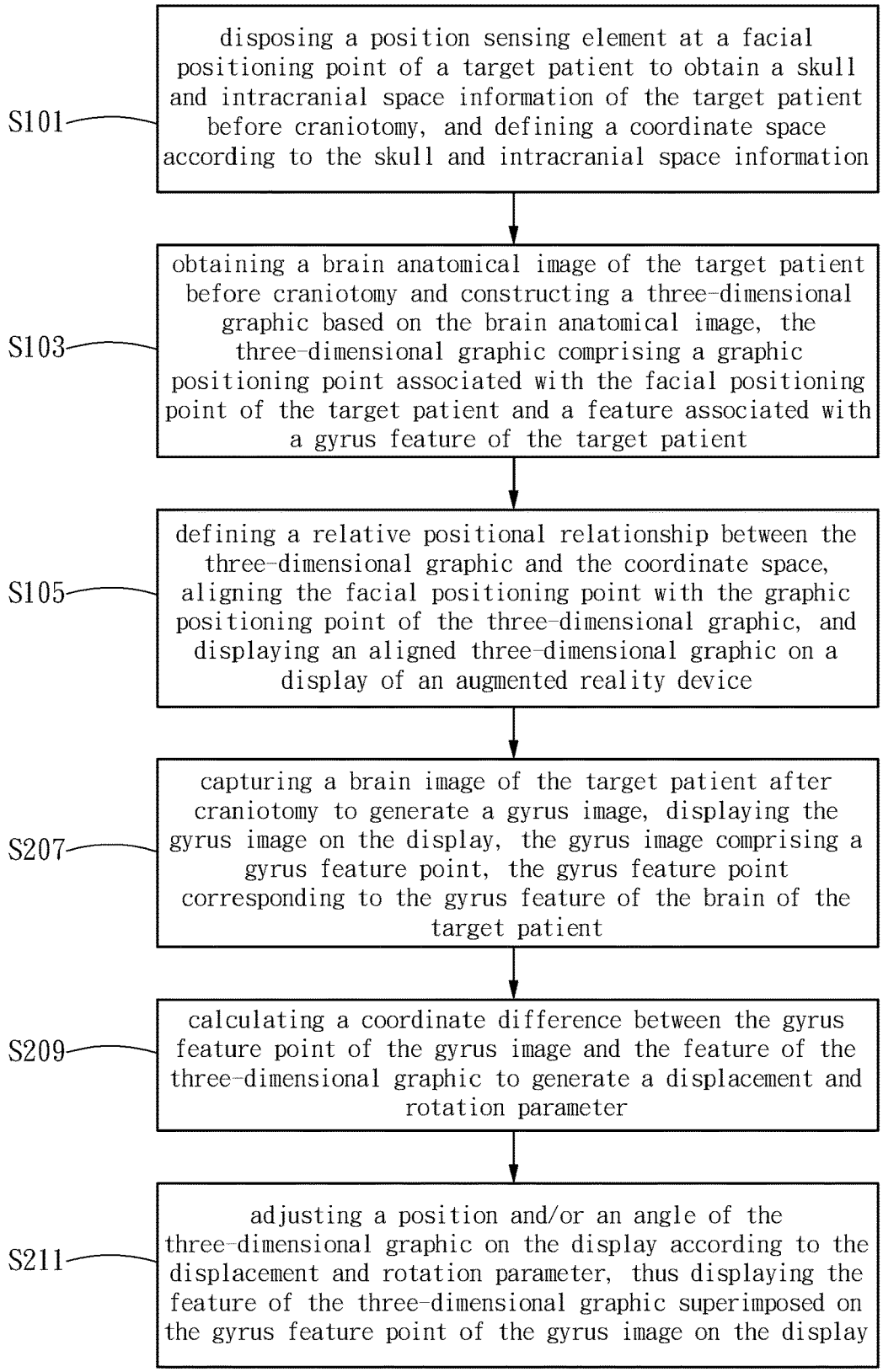
FIG. 11 is a flowchart of the method according to another embodiment of the invention.

Please refer to FIG. 11 for a flowchart of a method according to another embodiment of the invention. In a method 200 of this embodiment, steps S201 to S205 are the same as the aforementioned steps S101 to S105. In this embodiment, performing step S207 after step S205, when performing a surgical operation and during a craniotomy, using an imaging instrument to capture a brain image of the target patient 20 in the craniotomy, the brain image comprises a gyms image, and the imaging instrument, for example, can be a microscope for surgical operation (operating microscope or surgical microscope). Thereby, obtaining a position of the gyms feature of the brain of the target patient 20 during the surgical operation. In one example, obtaining a spatial position of the gyms feature in a preset coordinate system, the preset coordinate system can be defined based on the imaging instrument, and then converting the preset coordinate system into the coordinate space 30 to obtain a position of the gyrus feature in the coordinate space 30. Wherein, the gyms feature is defined as a calibration reference point.

The gyms image is displayed on the display 11a. Thereby, a user is capable of seeing the gyms image captured by the image capturing device 11b on the display 11a. In this embodiment, the gyrus image comprises a gyrus feature point, and the gyms feature point corresponds to the gyrus feature of the brain of the target patient 20.

In step S209, calculating a coordinate difference between the gyrus feature point of the gyrus image and the feature of the three-dimensional graphic 40a to generate a displacement and rotation parameter. The feature represents the graphic positioning point of the three-dimensional graphic 40a associated with the gyrus feature of the target patient 20, and the gyrus feature point is a feature point of the gyms image of the target patient 20 in the craniotomy captured through the image capturing device 11b. The displacement and rotation parameter generated through the coordinate difference comprises a coordinate difference between the feature and the gyms feature point. Thereby, the coordinate difference between the feature and the gyrus feature point can be calculated for using in subsequent positioning calibration of the three-dimensional graphic 40a.

Then, proceeding to step S211, adjusting a position and/or an angle of the three-dimensional graphic 40a on the display 11a according to the displacement and rotation parameter, thus displaying the feature of the three-dimensional graphic 40a superimposed on the gyms feature point of the gyrus image on the display 11a. The aforementioned various sensing, control and/or calculations can be implemented by the processing device 11c. Thereby, during a medical treatment operation, the system 10 is capable of calibrating the three-dimensional graphic 40a in real time, so that the display 11a is capable of displaying calibrated images.

Figure 12:
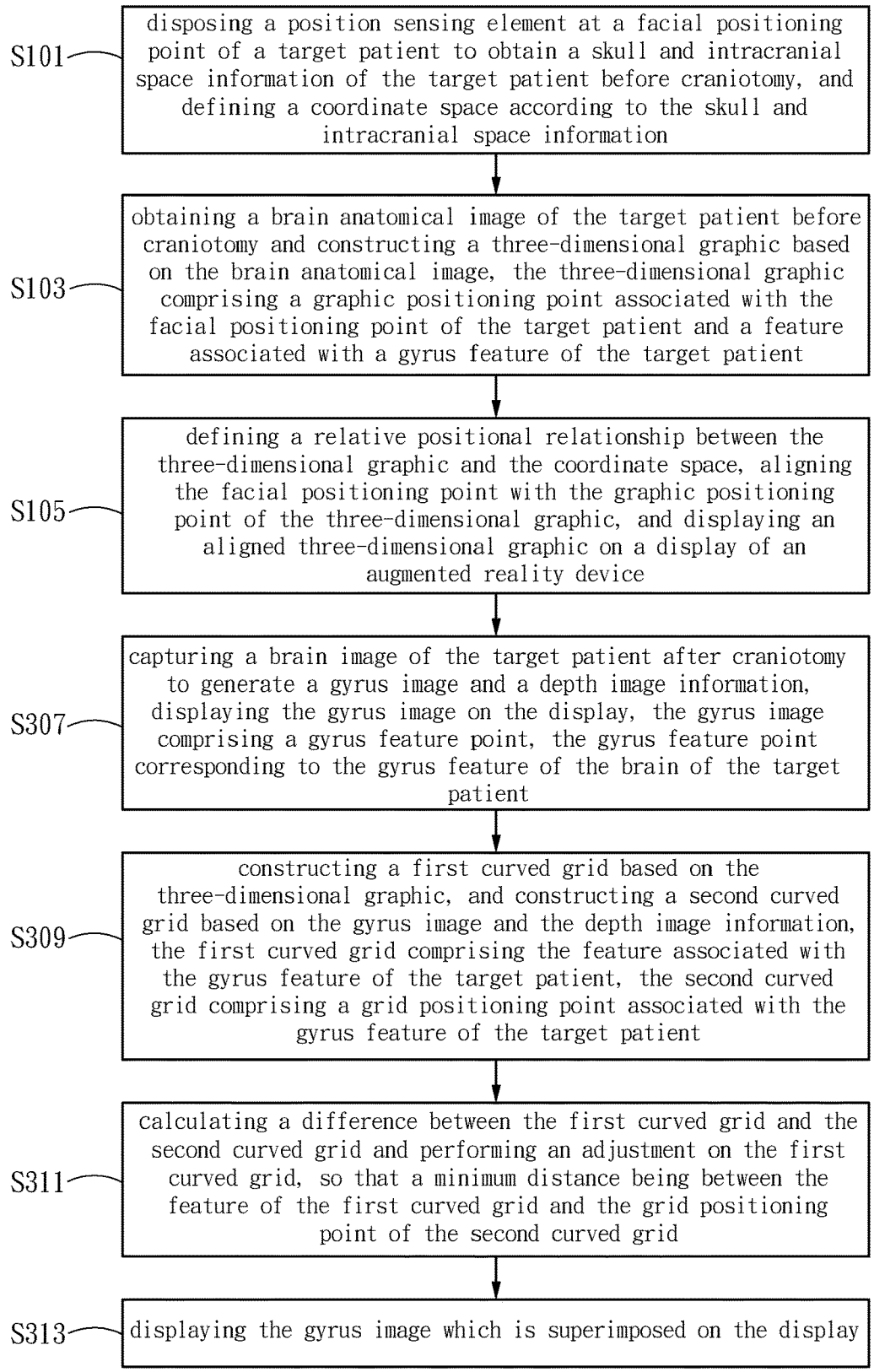
FIG. 12 is a flowchart of the method according to yet another embodiment of the invention.

Please refer to FIG. 12 for a flowchart of a method according to yet another embodiment of the invention. In a method 300 of this embodiment, steps S301 to S305 are the same as the aforementioned steps S101 to S105. In this embodiment, performing step S307 after step S305, after performing a craniotomy on the target patient 20 during a surgical operation, capturing a brain image of the target patient 20 in the craniotomy to generate a gyms image and a depth image information.

In this embodiment, capturing of the brain image can be realized by, for example, a multi-camera reconstruction technique; or capturing of the brain image can be realized by, for example, a depth camera composed of a camera and an infrared camera; or capturing of the brain image can be realized by, for example, using a camera-projector system with structured light projection-reconstruction. Thereby, the depth image information included in the captured brain image can have gyms depth information.

The gyms image is displayed on the display 11a of the augmented reality device 11. Thereby, the user is capable of seeing the gyms image captured by the image capturing device 11b on the display 11a. In this embodiment, the gyms image comprises a gyrus feature point, and the gyms feature point corresponds to the gyms feature of the brain of the target patient 20.

Figure 13A:
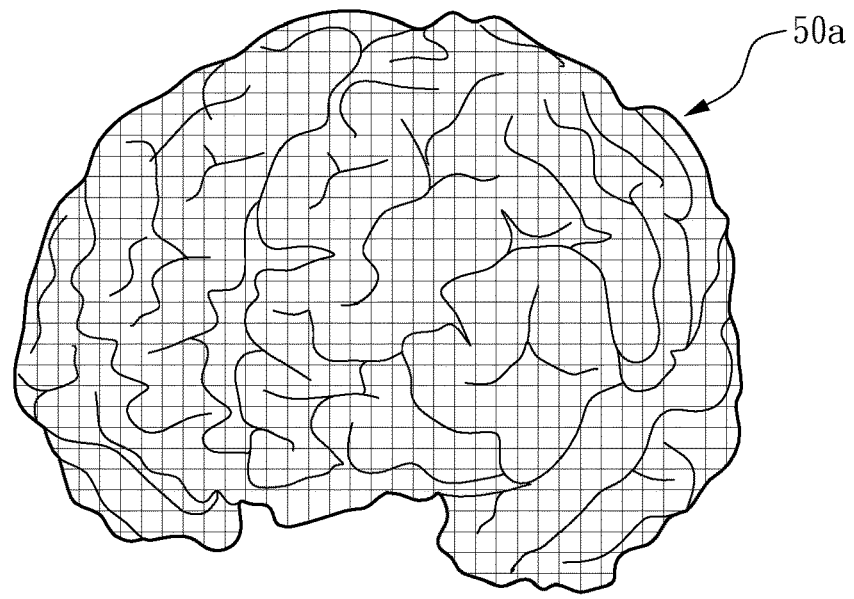
FIG. 13A and FIG. 13B are schematic diagrams of a first curved grid and a second curved grid according to an embodiment of the invention.
Figure 13B:
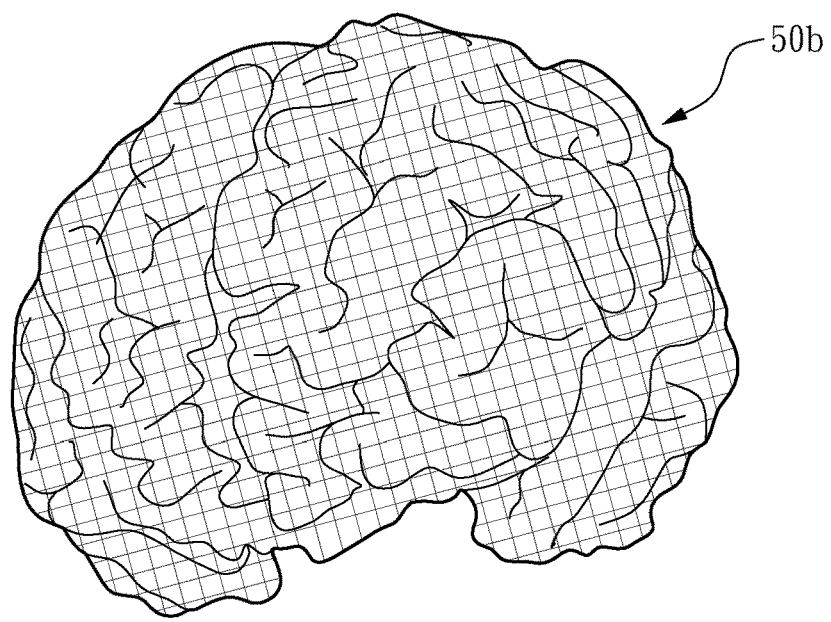

Then, referring to FIG. 13A and FIG. 13B, in step S309, constructing a first curved grid 50a based on the three-dimensional graphic 40a, and constructing a second curved grid 50b based on the gyms image and the depth image information, the first curved grid 50a comprising the feature associated with the gyrus feature of the target patient 20, and the second curved grid 50b comprising a grid positioning point associated with the gyms feature of the target patient 20.

Figure 14:
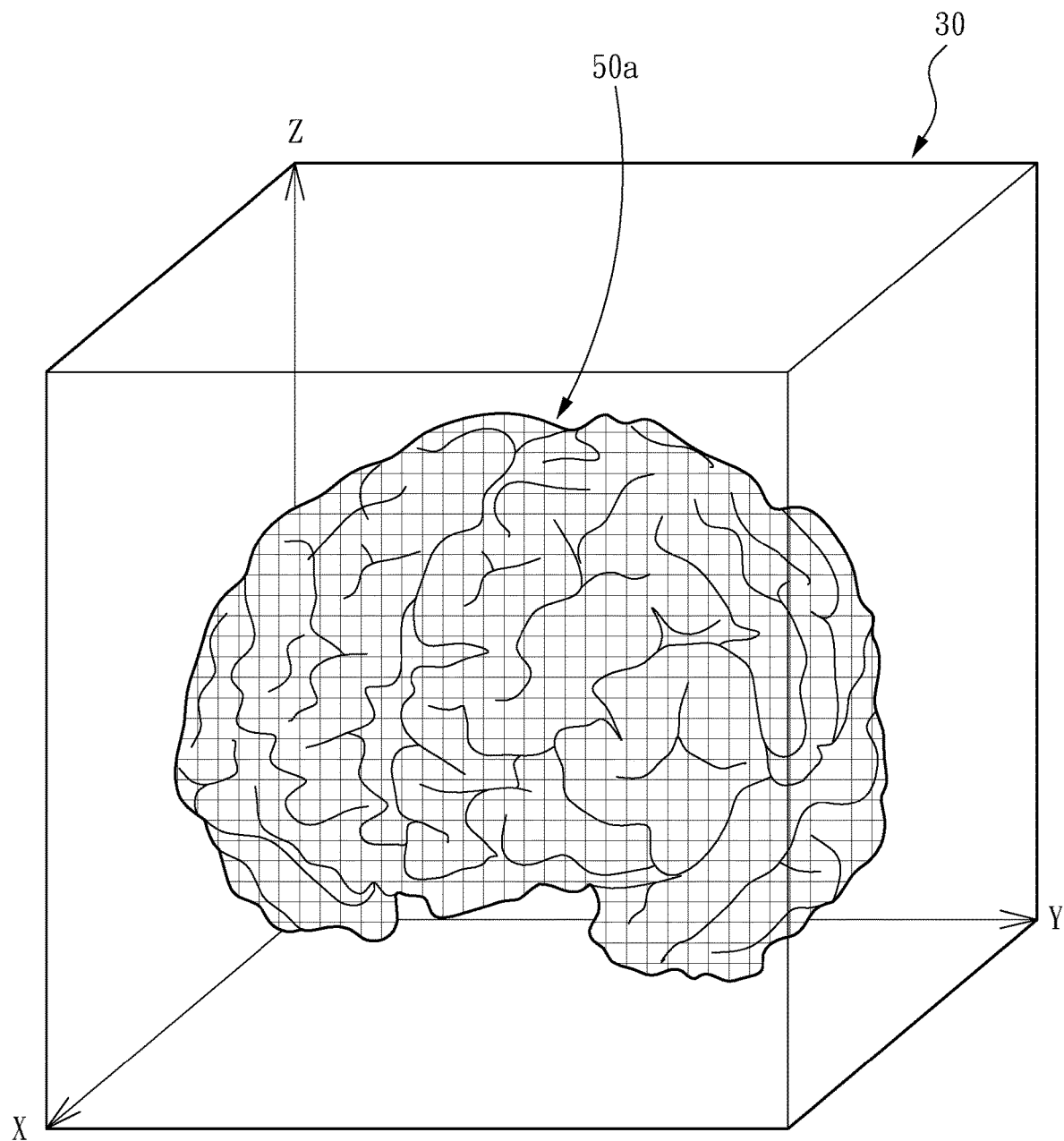
FIG. 14 is a schematic diagram of adjusting the first curved grid according to an embodiment of the invention.

Then, referring to FIG. 14, in step S311, calculating a difference between the first curved grid 50a and the second curved grid 50b and performing an adjustment on the first curved grid 50a, so that a minimum distance being between the feature of the first curved grid 50a and the grid positioning point of the second curved grid 50b. That is, calibrating the three-dimensional graphic 40a through the feature and the grid positioning point.

In detail, the feature represents the graphic positioning point of the three-dimensional graphic 40a associated with the gyms feature of the target patient 20, and the grid positioning point is the feature point of the gyrus image of the target patient 20 in the craniotomy captured through the image capturing device 11b. Thereby, the difference between the feature and the grid positioning point can be calculated for using in subsequent positioning calibration of the three-dimensional graphic 40a.

Then, in step S313, the display 11a displaying the superimposed gyrus image. The aforementioned various sensing, control and/or calculations can be implemented by the processing device 11c. Thereby, during a medical treatment operation, the system 10 is capable of calibrating the three-dimensional graphic 40a and the gyrus image in real time, so that the display 11a is capable of displaying calibrated images.

In addition, the system 10 can further comprise a physical workpiece, and the three-dimensional graphic 40a can further comprise a workpiece graphic. The workpiece graphic is a three-dimensional graphic corresponding to the workpiece in the three-dimensional graphic 40a, and medical treatment operations can be aided through the workpiece graphic. For example, the system 10 is capable of pre-displaying a position of the workpiece graphic on the display 11a to indicate possible subsequent medical treatment procedure and provide medical personnel for reference.

In addition, the workpiece can comprise position sensing elements, the position sensing elements are capable of providing position, direction, and angle information in space. The processing device 11c is capable of generating the workpiece graphic according to position signals generated by the position sensing elements. The position sensing elements can be realized by any possible positioning and displacement sensors. In one embodiment, the workpiece is illustrated with a scalpel as an example, but the invention is not limited thereto, nor does it limit a number of the workpiece. In other embodiments of the invention, the workpiece can comprise, for example, at least one feature point, and the system 10 generates the workpiece graphic through the feature point of the workpiece. The operating principle and details of the feature point of the workpiece can be similar to those of the aforementioned gyms feature of the target patient 20, and thus will not be repeated herein.

In this embodiment, the three-dimensional graphic 40a can further comprise, for example, at least one indicating graphic. For example, the indicating graphic can correspond to a medical treatment procedure to aid in a medical treatment, and disposition of the indicating graphic is capable of auxiliary in medical treatment operations. For example, the indicating graphic can be provided for indication of a next position of using a scalpel in a surgical operation.

In summary, the augmented reality-assisted method for performing surgery of the invention uses the displacement and rotation parameter obtained in the craniotomy to adjust the three-dimensional graphic displayed on the display of the augmented reality device, so that the three-dimensional graphic and the feature of brain of the target patient are aligned with each other to ensure that the three-dimensional graphic on the display matches with the brain of the target patient; or adjust the difference between the first curved grid constructed based on the three-dimensional graphic and the second curved grid constructed based on the gyms image and the depth image information in order to allow doctors to be capable of accurately pinpointing the symptoms. Therefore, calibrated images can be provided in real time and accurately for using in supporting medical treatment, surgery, or operating instruments.

Note that the specification relating to the above embodiments should be construed as exemplary rather than as limitative of the present invention, with many variations and modifications being readily attainable by a person of average skill in the art without departing from the spirit or scope thereof as defined by the appended claims and their legal equivalents.

What is claimed is:

1. An augmented reality-assisted method for performing surgery comprising following steps of:
    step 1: disposing a first position sensing element at a facial positioning point of a target patient to obtain a skull space information and an intracranial space information of the target patient before craniotomy, and defining a coordinate space according to the skull space information and the intracranial space information;
    step 2: obtaining a brain anatomical image of the target patient before craniotomy and constructing a three-dimensional graphic based on the brain anatomical image, the three-dimensional graphic comprising a graphic positioning point associated with the facial positioning point of the target patient and a feature associated with a gyrus feature of the target patient;
    step 3: placing the three-dimensional graphic in the coordinate space, aligning the facial positioning point with the graphic positioning point of the three-dimensional graphic, and displaying an aligned three-dimensional graphic on a display of an augmented reality device;
    step 4: using a probe to obtain a spatial position of the gyrus feature of the target patient in the coordinate space after craniotomy, using the gyrus feature as a calibration reference point;
    step 5: generating a displacement and rotation parameter based on a coordinate difference of the feature of the three-dimensional graphic relative to the calibration reference point; and
    step 6: adjusting a position and/or an angle of the three-dimensional graphic on the display according to the displacement and rotation parameter, so that the display displaying a calibrated three-dimensional graphic.

2. The method as claimed in claim 1, wherein the three-dimensional graphic is generated from a plurality of multi-section nuclear magnetic resonance images through a volume rendering, and the multi-section nuclear magnetic resonance images are generated by a nuclear magnetic resonance imaging (NMRI) device that detects a target object.

3. The method as claimed in claim 1, wherein the three-dimensional graphic further comprises a workpiece graphic, the workpiece graphic corresponds to a workpiece, the workpiece comprises at least one second position sensing element, and a processing device of the augmented reality device generates the workpiece graphic according to at least one position signal generated by the at least one second position sensing element.

4. The method as claimed in claim 1, wherein the three-dimensional graphic further comprises at least one indicating graphic, and the indicating graphic corresponds to a medical treatment procedure.

5. An augmented reality-assisted method for performing surgery, comprising following steps of:
   step 1: disposing a first position sensing element at a facial positioning point of a target patient to obtain a skull and intracranial space information of the target patient before craniotomy, and defining a coordinate space according to the skull and intracranial space information;
   step 2: obtaining a brain anatomical image of the target patient before craniotomy and constructing a three-dimensional graphic based on the brain anatomical image, the three-dimensional graphic comprising a graphic positioning point associated with the facial positioning point of the target patient and a feature associated with a gyrus feature of the target patient;
   step 3: defining a relative positional relationship between the three-dimensional graphic and the coordinate space, aligning the facial positioning point with the graphic positioning point of the three-dimensional graphic, and displaying an aligned three-dimensional graphic on a display of an augmented reality device;
   step 4: capturing a brain image of the target patient after craniotomy to generate a gyrus image, displaying the gyrus image on the display, the gyrus image comprising a gyrus feature point, the gyrus feature point corresponding to the gyrus feature of the brain of the target patient;
   step 5: calculating a coordinate difference between the gyrus feature point of the gyrus image and the feature of the three-dimensional graphic to generate a displacement and rotation parameter; and
   step 6: adjusting a position and/or an angle of the three-dimensional graphic on the display according to the displacement and rotation parameter, thus displaying the feature of the three-dimensional graphic superimposed on the gyrus feature point of the gyrus image on the display.

6. The method as claimed in claim 5, wherein the three-dimensional graphic is generated from a plurality of multi-section nuclear magnetic resonance images through a volume rendering, and the multi-section nuclear magnetic resonance images are generated by a nuclear magnetic resonance imaging (NMRI) device that detects a target object.

7. The method as claimed in claim 5, wherein the three-dimensional graphic further comprises a workpiece graphic, the workpiece graphic corresponds to a workpiece, the workpiece comprises at least one second position sensing element, and a processing device of the augmented reality device generates the workpiece graphic according to at least one position signal generated by the at least one second position sensing element.

8. The method as claimed in claim 5, wherein the three-dimensional graphic further comprises at least one indicating graphic, and the indicating graphic corresponds to a medical treatment procedure.

9. An augmented reality-assisted method for performing surgery, comprising following steps of:
   step 1: disposing a first position sensing element at a facial positioning point of a target patient to obtain a skull and intracranial space information of the target patient before craniotomy, and defining a coordinate space according to the skull and intracranial space information;
   step 2: obtaining a brain anatomical image of the target patient before craniotomy and constructing a three-dimensional graphic based on the brain anatomical image, the three-dimensional graphic comprising a graphic positioning point associated with the facial positioning point of the target patient and a feature associated with a gyrus feature of the target patient;
   step 3: defining a relative positional relationship between the three-dimensional graphic and the coordinate space, aligning the facial positioning point with the graphic positioning point of the three-dimensional graphic, and displaying an aligned three-dimensional graphic on a display of an augmented reality device;
   step 4: capturing a brain image of the target patient after craniotomy to generate a gyrus image and a depth image information, displaying the gyrus image on the display, the gyrus image comprising a gyrus feature point, the gyrus feature point corresponding to the gyrus feature of the brain of the target patient;
   step 5: constructing a first curved grid based on the three-dimensional graphic, and constructing a second curved grid based on the gyrus image and the depth image information, the first curved grid comprising the feature associated with the gyrus feature of the target patient, the second curved grid comprising a grid positioning point associated with the gyrus feature of the target patient;
   step 6: calculating a difference between the first curved grid and the second curved grid and performing an adjustment on the first curved grid, so that a minimum distance being between the feature of the first curved grid and the grid positioning point of the second curved grid; and
   step 7: displaying the gyrus image which is superimposed on the display.

10. The method as claimed in claim 9, wherein the three-dimensional graphic is generated from a plurality of multi-section nuclear magnetic resonance images through a volume rendering, and the multi-section nuclear magnetic resonance images are generated by a nuclear magnetic resonance imaging (NMRI) device that detects a target object.

11. The method as claimed in claim 9, wherein the three-dimensional graphic further comprises a workpiece graphic, the workpiece graphic corresponds to a workpiece, the workpiece comprises at least one second position sensing element, and a processing device of the augmented reality device generates the workpiece graphic according to at least one second position signal generated by the at least one position sensing element.

12. The method as claimed in claim 9, wherein the three-dimensional graphic further comprises at least one indicating graphic, and the indicating graphic corresponds to a medical treatment procedure.

\* \* \* \* \*